United States Patent
Deola

(10) Patent No.: US 9,295,580 B1
(45) Date of Patent: Mar. 29, 2016

(54) HEATED DISPOSABLE GLOVES

(75) Inventor: James A. Deola, Milmay, NJ (US)

(73) Assignee: Paul Deola, III, Vineland, NJ (US), part interest ( * ) Notice: Subject to any disclaimer, the term of this patent is extended or adjusted under 35 U.S.C. 154(b) by 916 days.

(21) Appl. No.: 13/136,691

(22) Filed: Aug. 8, 2011

(51) Int. Cl.
*A61F 7/03* (2006.01)
*F24J 1/00* (2006.01)

(52) U.S. Cl.
CPC . *A61F 7/034* (2013.01); *A61F 7/03* (2013.01); *F24J 1/00* (2013.01)

(58) Field of Classification Search
CPC ............... A61F 7/03; A61F 7/034; F24J 1/00
USPC ................................. 126/204, 263.01, 263.02
See application file for complete search history.

(56) References Cited

U.S. PATENT DOCUMENTS

| | | | |
|---|---|---|---|
| 1,970,081 A * | 8/1934 | Eisendrath ..................... | 126/204 |
| 4,535,482 A | 8/1985 | Spector et al. | |
| 5,035,003 A | 7/1991 | Rinehart | |
| 5,541,388 A * | 7/1996 | Gadd ............................. | 219/211 |
| 6,116,231 A * | 9/2000 | Sabin et al. ............... | 126/263.01 |
| 2004/0112366 A1* | 6/2004 | Addison et al. ............... | 126/204 |
| 2008/0000890 A1* | 1/2008 | Chen ............................. | 219/211 |
| 2008/0255645 A1* | 10/2008 | Nakamura ..................... | 607/108 |
| 2009/0057290 A1* | 3/2009 | Williams ...................... | 219/211 |
| 2009/0188905 A1* | 7/2009 | Williams ...................... | 219/211 |
| 2009/0242539 A1* | 10/2009 | Wassel .......................... | 219/240 |
| 2013/0220297 A1* | 8/2013 | Sivucka et al. ............... | 126/204 |

\* cited by examiner

*Primary Examiner* — Gregory Huson
*Assistant Examiner* — Aaron Heyamoto
(74) *Attorney, Agent, or Firm* — Norman E. Lehrer

(57) ABSTRACT

A disposable heated glove for heating a wearer's hand includes a fabric material for covering the palm and back of the hand, four finger portions for covering the wearer's fingers and a thumb portion for covering the wearer's thumb. The glove also includes five small elongated pouches with each pouch being associated with a different one of the finger and thumb portions. A quantity of exothermic chemicals is sealed within each of the pouches whereby removing chemicals from one of the pouches results in the destruction of the pouch so that it cannot be reused. In one embodiment, the chemicals are activated to create heat by manually manipulating the same to mix the chemicals. In another embodiment, the chemicals are activated by exposing them to the atmosphere.

4 Claims, 2 Drawing Sheets

US 9,295,580 B1

HEATED DISPOSABLE GLOVES

BACKGROUND OF THE INVENTION

The present invention is directed toward heated gloves and more particularly, toward inexpensive gloves with chemical heaters integrally formed therewith and which are intended to be disposable after a single use.

There are numerous times when it is necessary or simply desirable to wear heated gloves. Workers who must be outside on cold days, skiers or spectators at winter sporting events would benefit substantially from the same. Over the years, various types of heated groves have been proposed but to Applicant's knowledge none has been successful. This is probably due to the high cost of prior art gloves.

Attempts to produce heated gloves have included electric heating elements within the gloves which requires a power source such as batteries carried by the gloves or on the person's body separate from the gloves. In either case, the batteries cannot last very long as electric heating elements draw a great deal of current and drain batteries very quickly.

Exothermic chemical packs have also been proposed for use as a heat source for heating gloves. In every case known to Applicant, the gloves include one or more pouches into which a chemical heat pack can be inserted. Some of the gloves then transmit the heat from the heat pack through conductive material such as shown in FIGS. 1 and 6 of U.S. Pat. No. 4,535,482 to Spector et al. or through the use of various liquid bladders such as shown in U.S. Pat. No. 5,035,003 to Rinehart.

After the chemical heat packs are exhausted, they are removed from the pouches attached to the gloves and are discarded. New heat packs can then be inserted into the pouches. While such gloves may be useful, they can also be expensive as they must be provided with pouches that can be opened and closed. The gloves can also be somewhat bulky.

Thus, there is a need for an inexpensive heated glove and particularly one that can be used by itself or as a glove liner or insert that can be used with an outer glove.

SUMMARY OF THE INVENTION

The present invention is designed to overcome the deficiencies of the prior art discussed above. It is an object of the present invention to provide a self contained heated glove.

It is another object of the present invention to provide a self contained heated glove that is inexpensive and disposable.

It is an even further object of the present invention to provide a self contained disposable heated glove that can also be used as a glove liner.

In accordance with illustrative embodiments demonstrating features and advantages of the present invention, there is provided a disposable heated glove for heating a wearer's hand that includes a fabric material for covering the palm and back of the hand, four finger portions for covering the wearer's fingers and a thumb portion for covering the wearer's thumb. The glove also includes five small elongated pouches with each pouch being associated with a different one of the finger and thumb portions. A quantity of exothermic chemicals is sealed within each of the pouches whereby removing chemicals from one of the pouches results in the destruction of the pouch so that it cannot be reused. In one embodiment, the chemicals are activated to create heat by manually manipulating the same to mix the chemicals. In another embodiment, the chemicals are activated by exposing them to the atmosphere.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form that is presently preferred; it being understood that the invention is not intended to be limited to the precise arrangements and instrumentalities shown.

DETAILED DESCRIPTION OF THE PREFERRED EMBODIMENT

Figure 1:
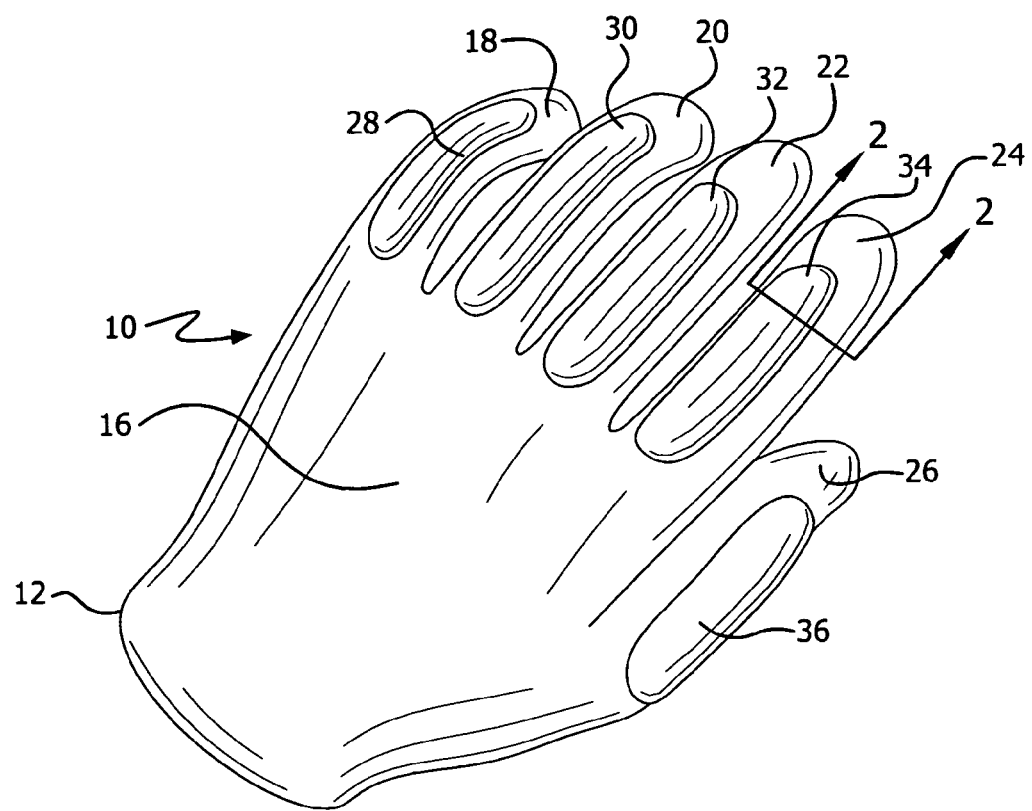
FIG. 1 is a perspective view of a disposable heated glove of the present invention.

Referring now to the drawings in detail wherein like reference numerals have been used throughout the various figures to designate like elements, there is shown in FIG. 1 a disposable heated glove constructed in accordance with the principles of the present invention and designated generally as 10. The major portions of the glove 10 are constructed in a conventional manner well known in the art. It is made from a fabric material 12 that has a palm portion 14 (see FIG. 3) that is intended to cover the palm of a person's hand and a back portion 16 that is intended to cover the back of a person's hand.

There are also four finger portions 18, 20, 22 and 24 for covering the wearer's fingers and a thumb portion 26 for covering the wearer's thumb. Again, the glove thus far described is, per se, conventional in the art.

The material 12 from which the glove is made may be latex, polyvinyl chloride, polyurethane or any other plastics material. Alternatively, the glove could be made from a paper like or nonwoven material. It is also possible to make the glove from a woven material or combinations of any of these materials. What is important to the present invention is that the glove be made of a material so that the same is extremely inexpensive. The glove of the present invention is intended to be worn once and then disposed of.

Integrally formed with each of the finger portions and thumb portion are elongated pouches such as shown at 28, 30, 32, 34 and 36. These pouches may be made of the same material as the glove or of a different material. The pouches can be secured to the finger portions in any known manner such as through the use of an adhesive or glue or some type of thermal process. It is also possible to make the pouches separately so as to be self contained with an adhesive layer thereon which can be attached to the various portions of the glove.

Figure 3:
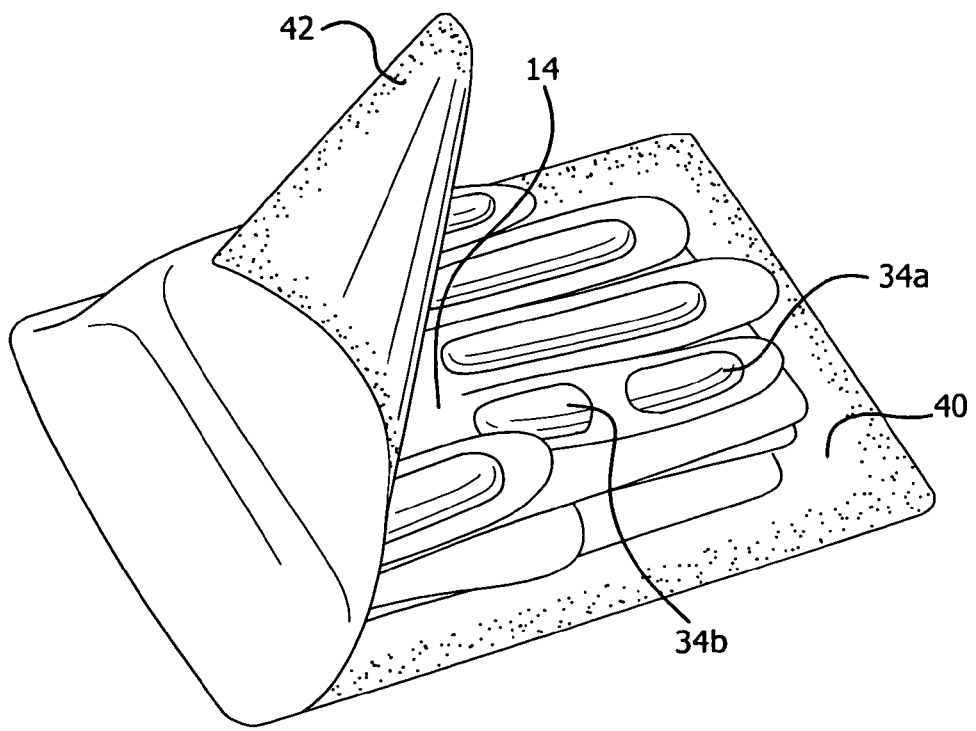
FIG. 3 is a perspective view illustrating one manner in which the glove of the invention can be packaged for sale.

As shown in FIG. 1, the pouches are mounted to or otherwise associated with the back of the fingers. It is also possible to mount them to the front of the finger portions as shown in FIG. 3. In addition, two or more pouches could be associated with each finger portion such as shown at 34a and 34b in FIG. 3. Multiple pouches can be placed anywhere on the fingers such as one on the back and one on the front or on the sides. Even further, in some cases, it may not be necessary or desirable to utilize a pouch on each of the finger portions and thumb portion.

Figure 2:
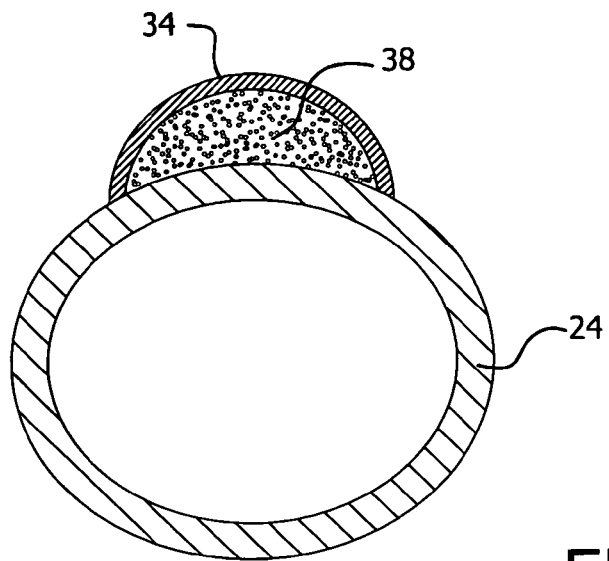
FIG. 2 is a cross-sectional view of a finger portion taken through the line 2-2 of FIG. 1.

Located within each of the pouches is a quantity of exothermic chemicals such as shown at 38 in FIG. 2. Such chemicals 38 are, per se, well known in the art and are commonly used in various types of heat packs readily available. As is well known in the art, the chemicals 38 have different ingredients that are initially separated from each other. Manually squeezing, twisting or otherwise manipulating the same to cause the various ingredients to mix creates heat which is transmitted from the pouches through the finger portions to the wearer's fingers.

The foregoing is, of course, by way of example only. Other exothermic chemicals can also be used in lieu of those discussed above. For example, it is known that certain chemicals produce heat when exposed to the atmosphere. If such chemicals are utilized, either the pouch 34 or the material 12 from which the glove is made can be porous or have holes formed in the proper locations to allow air to pass therethrough and react with the chemicals 38.

If air-activated chemicals 38 are utilized, the glove 12 could then be sold in a package such as shown in FIG. 3. One or more gloves would be sealed in an airtight package between a bottom packaging sheet 40 and a top cover packaging sheet 42. When it is desired to utilize the gloves 10, the top sheet 42 is removed from the bottom sheet 40 exposing the gloves and chemicals 38 therein to the air which would activate the heat. Alternatively, the pouches could have holes strategically placed therein which are covered by separate covers that could be removed to expose the contents to the air.

In lieu of the packaging shown in FIG. 3, one or more pairs of gloves could be packaged in a plastic bag. The bag could be airtight and sealed so that the chemicals 38 are activated when the bag is opened and the gloves are exposed to the air. Alternatively, and as described above, the chemicals 38 could be activated before or after the gloves are removed from the bag by manually manipulating the pouches.

The gloves 10 of the present invention could be used by themselves to be worn by anyone wishing to keep his or her hands warm. Because it is the extremities of a person's hands, i.e. his or her fingers or thumb that tend to get cold, the heating elements are preferably applied to the fingers. It is not beyond the scope of the present invention, however, to utilize the gloves 10 as glove liners. That is, a person will first put the glove 10 on and then insert the gloved hand into another outer glove. In any event, the gloves are intended to be used only once and then disposed of. The pouches cannot be opened to remove the chemicals in order to replace them as removing a pouch or attempting to expose the chemicals would destroy the glove.

The present invention may be embodied in other specific forms without departing from the spirit or essential attributes thereof and accordingly, reference should be made to the appended claims rather than to the foregoing specification as indicating the scope of the invention.

I claim:

1. A disposable heated glove for heating a wearer's hand including a fabric material for covering the palm and back of the hand, four finger portions for covering the wearer's fingers and a thumb portion for covering the wearer's thumb, the improvement comprising: a plurality of small pouches, each of said pouches being associated with a different one of said finger and thumb portions and being integrally formed therewith, and a quantity of exothermic chemicals sealed within each of said pouches whereby removing said chemicals from one of said pouches results in the destruction of said one of said pouches so that it cannot be reused.

2. The disposable heated glove for heating a wearer's hand as claimed in claim 1 including five pouches.

3. The disposable heated glove for heating a wearer's hand as claimed in claim 1 wherein said chemicals are activated by manually manipulating the chemicals to mix them.

4. The disposable heated glove for heating a wearer's hand as claimed in claim 1 wherein said chemicals are activated by exposing them to the atmosphere.

* * * * *